US00PP19811P2

(12) United States Plant Patent
Bailey

(10) Patent No.: US PP19,811 P2
(45) Date of Patent: Mar. 10, 2009

(54) ***CELASTRUS* PLANT NAMED 'BAILUMN'**

(50) Latin Name: *Celastrus scandens*
Varietal Denomination: Bailumn

(75) Inventor: Rodney Bailey, Woodbury, MN (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 12/148,452

(22) Filed: Apr. 18, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L Bell
(74) *Attorney, Agent, or Firm*—Penny J. Aguirre

(57) ABSTRACT

A new cultivar of *Celastrus scandens,* 'Bailumn', characterized by its production of primarily perfect flowers with heavy production of large fruit without the need for planting both male and female plants. 'Bailumn' is further characterized by its vigorous growth and ability to grow in a wide range of growing conditions with hardiness in U.S.D.A. Zones 2 to 8 and tolerance to drought.

3 Drawing Sheets

Botanical classification: *Celastrus scandens.*
Variety denomination: 'Bailumn'.

BACKGROUND OF THE INVENTION

The present invention relates to a new and distinct cultivar of *Celastrus scandens* will be referred to hereafter by its cultivar name, 'Bailumn'. 'Bailumn' a new cultivar of American bittersweet, a vine grown for use as an ornamental landscape plant and for use in the floral market as cut branches.

The inventor discovered 'Bailumn' as a naturally occurring whole plant mutation of an unnamed plant of *Celastrus scandens* in summer of 2002 in a cultivated garden in St. Paul, Minn.

Asexual reproduction of the new cultivar was first accomplished under the direction of the inventor using softwood stem cuttings in summer of 2003 in St. Paul, Minn. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for four years in St. Paul, Minn. These attributes in combination distinguish 'Bailumn' as a unique cultivar of American bittersweet.

1. 'Bailumn' exhibits large fruit; about twice the size as the parent species.
2. 'Bailumn' exhibits a heavy production of fruit that are borne on large terminal panicles.
3. 'Bailumn' produces primarily perfect flowers, a characteristic that is unique as the parent species is typically polygamo-dioecious. 'Bailumn' will produce fruit when planted as a single plant.

4. 'Bailumn' is a vigorous grower, is hardy is U.S.D.A. Zones 2 to 8, is drought tolerant, and will grow in a wide range of growing conditions.

The parent species, *Celastrus scandens,* is the only comparison plant known to the inventor. 'Bailumn' differs in having primarily perfect flowers (60 to 75%), whereas the species is primarily polygamo-dioecious and requires both male and female plants for fruit set. 'Bailumn' also has larger fruit, increased fruit set, and larger panicles of fruit than *Celastrus scandens.*

BRIEF DESCRIPTION OF THE DRAWING

The accompanying colored photographs illustrate the overall appearance and distinct characteristics of 4 year-old plants the new American bittersweet as grown in St. Paul, Minn. The colors in the photographs are as close as possible with the digital photography techniques available, the color values cited in the detailed botanical description accurately describe the colors of the new American bittersweet.

DETAILED BOTANICAL DESCRIPTION

Figure 1:
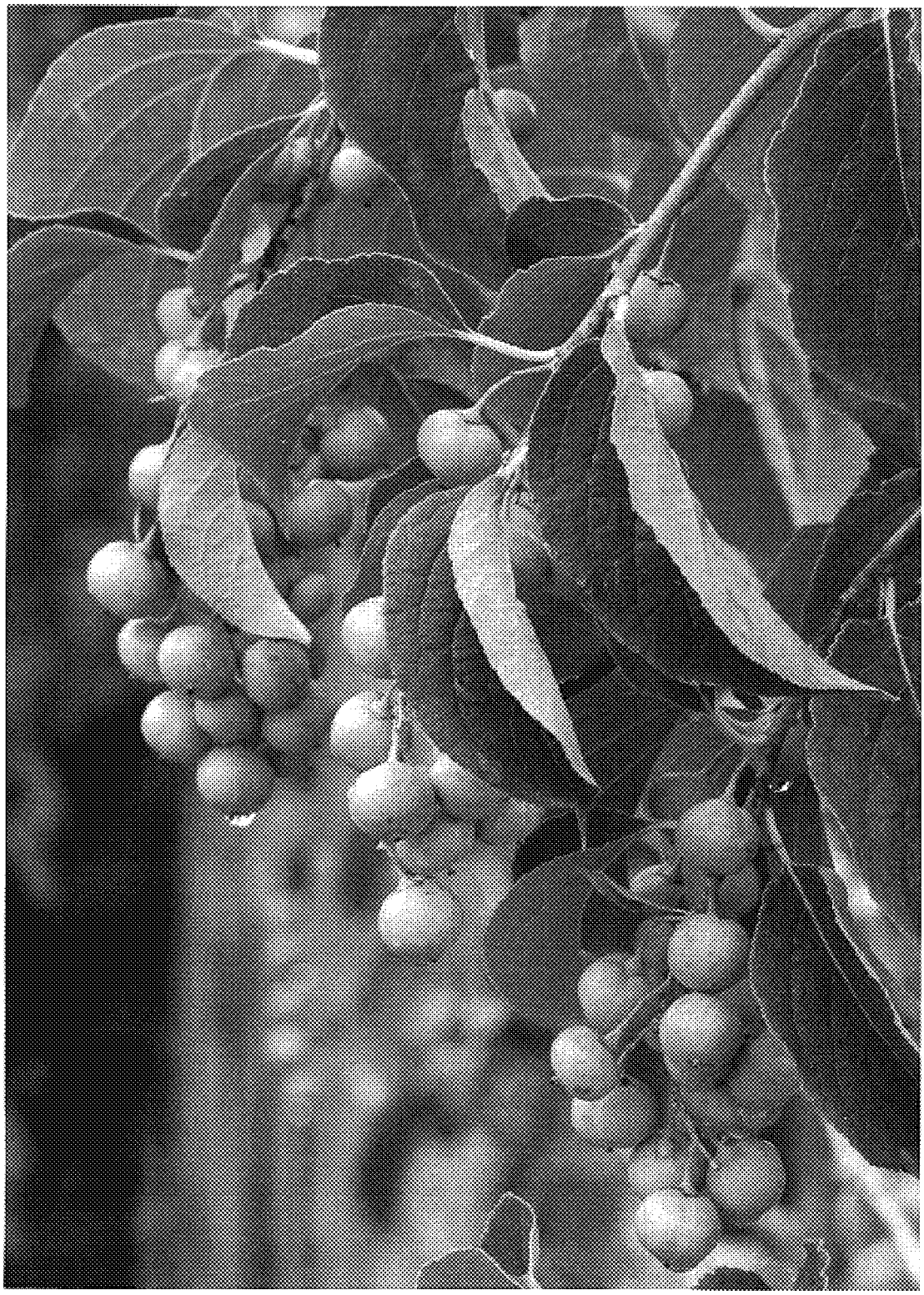
FIG. 1 provides a close-up of the foliage and fruit in mid summer.
Figure 2:
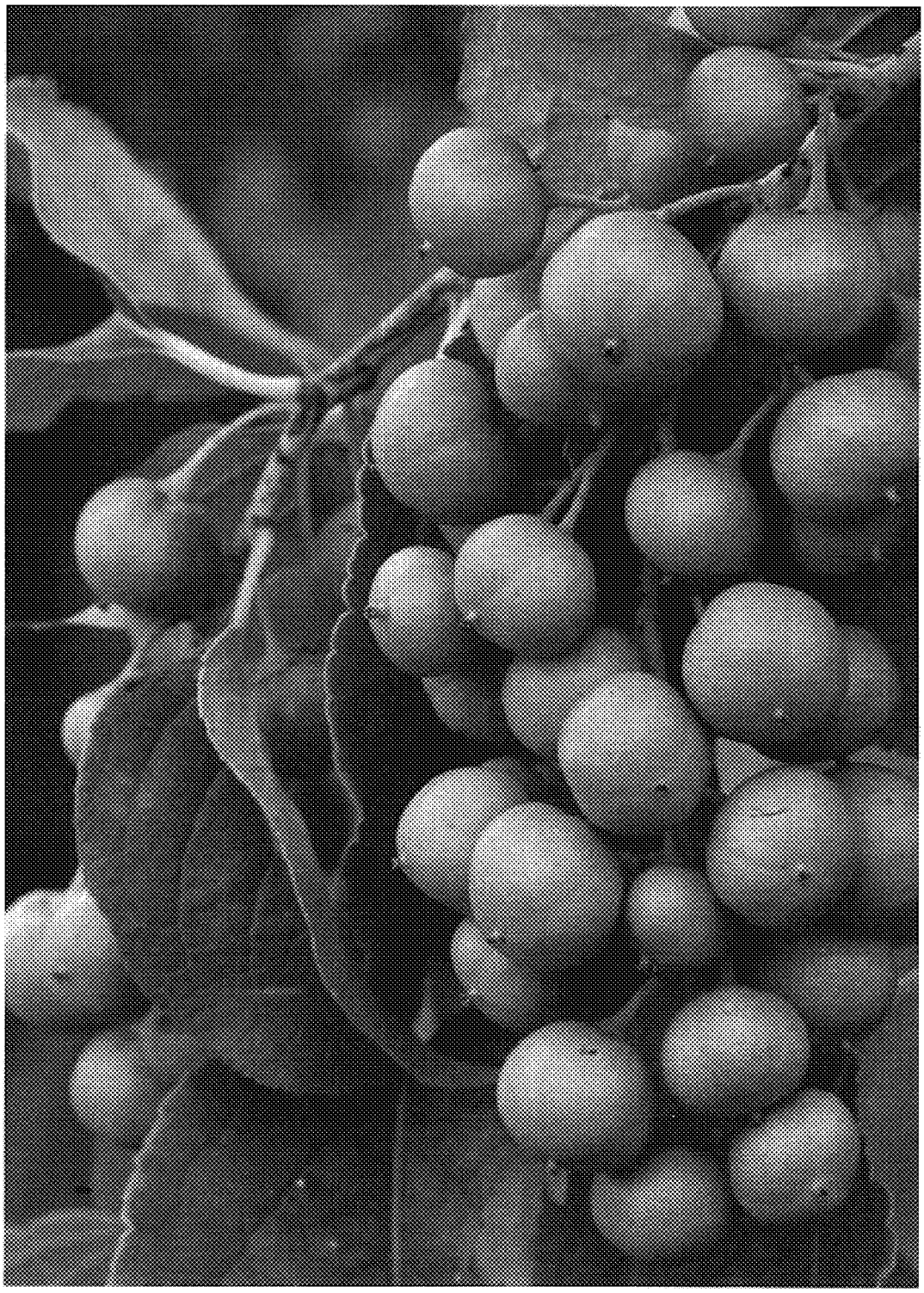
FIG. 2 provides a close-up view of a panicle of fruit in late summer.
Figure 3:
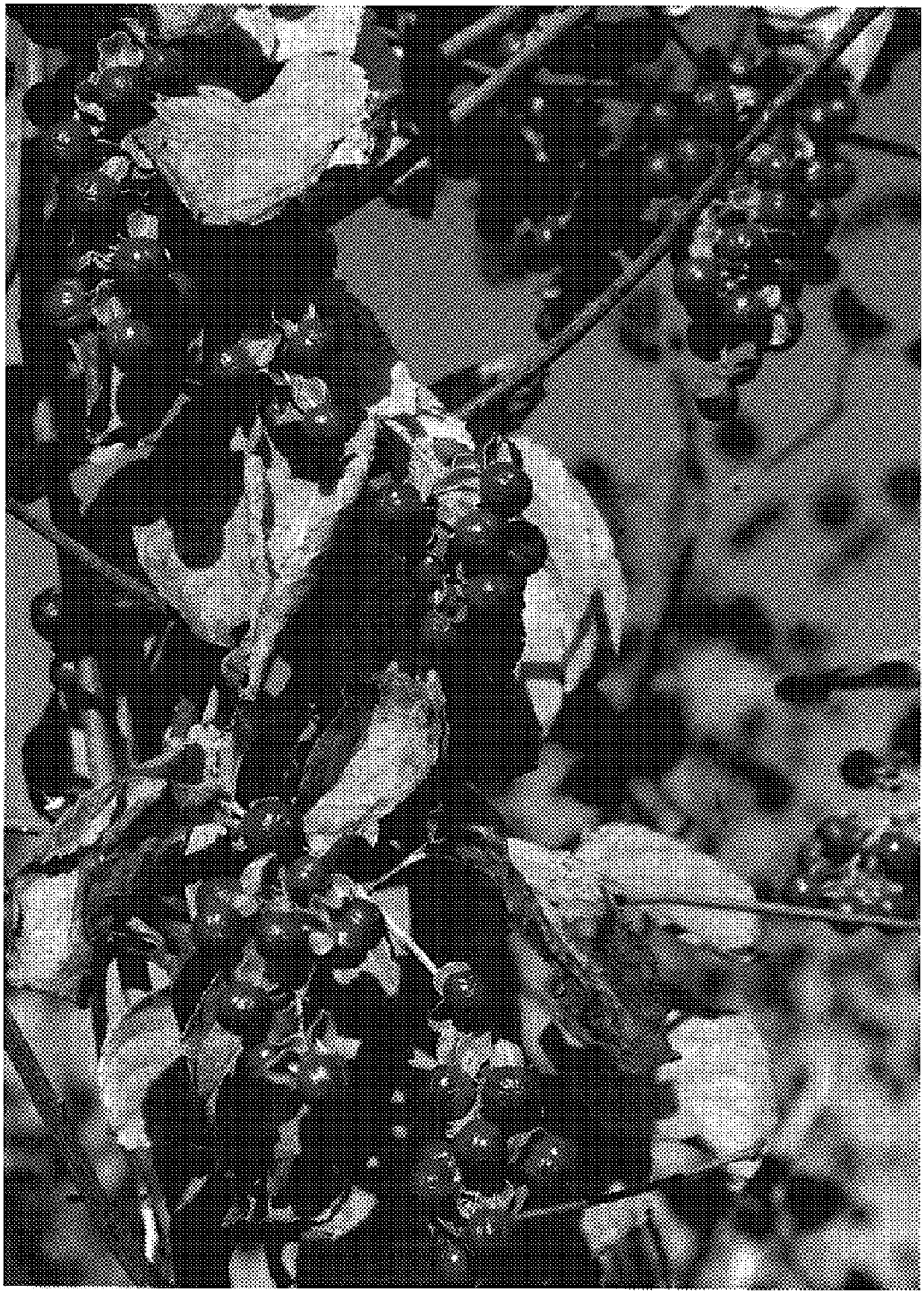
FIG. 3 provides a view of the seed capsules in fall with arils exposed.

The following is a detailed description of the new cultivar as grown outdoors in full sun in a trial plot in St. Paul, Minn. for 4 years. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms for about 2 weeks in early summer with some repeat bloom in mid summer.

*Plant habit.*—Twining vine, growth is prostrate unless supported.

*Length.*—Reaches up to 7 m in length.

*Cold hardiness.*—U.S.D.A. Zones 2 to 8.

*Diseases and pests.*—No susceptibility or resistance to diseases or pests has been observed.

*Culture.*—Grows in wide range of soil conditions in full sun, drought tolerant.

*Root description.*—Fibrous.

Growth and propagation:

*Propagation.*—Terminal, softwood stem cuttings.

*Growth rate.*—Vigorous.

Stem description:

*Shape.*—Oval.

*Stem color.*—New growth emerges 144A, mature wood color between N200A and N200B with coating of N200C and lenticels 161D.

*Stem size.*—Main stems; 7 mm in diameter and up to 7.5 m in length, flowering lateral branches; average of 4 mm in diameter and 1 m in length.

*Stem surface.*—Glabrous, new growth is satiny, mature wood is dull and ridged.

*Internode length.*—Typically 3 to 5 cm.

*Branching.*—Average of 8 lateral branches per main stem 1.5 m in length.

Foliage description:

*Leaf shape.*—Oval.

*Leaf division.*—Simple.

*Leaf base.*—Broadly cuneate.

*Leaf apex.*—Acuminate to mucronate.

*Leaf fragrance.*—None.

*Leaf venation.*—Odd-pinnate, not prominent, midrib is conspicuous on lower surface only, 144B in color.

*Leaf margins.*—Serrulate.

*Leaf arrangement.*—Alternate.

*Leaf attachment.*—Petiolate.

*Leaf surface.*—Glabrous on upper and lower surface.

*Leaf internode length.*—Average of 2.5 cm.

*Leaf size.*—Average of 9 cm in length and 5.5 cm in width.

*Leaf quantity.*—Average 24 per branch 60 cm in length.

*Leaf color.*—Newly expanded leaves; upper surface 137C, lower surface 138A, mature leaves; upper surface 137A, lower surface color 137B, fall leaves; upper and lower surface 151C to 154A.

*Petioles.*—About 1.2 cm in length, 2 mm in width, 144A in color, glabrous surface.

*Stipules.*—Not present.

Inflorescence description:

*Inflorescence type.*—Terminal panicles on lateral branches.

*Flower buds.*—Conical in shape, 144A in color with tips 151A, 4 mm in length and 2 mm in width.

*Flower fragrance.*—None detected.

*Lastingness of inflorescence.*—Panicle blooms for about 2 weeks.

*Flower quantity.*—Average of 37 flowers per terminal panicle and 3 per laterals.

*Flower type.*—Rotate, 5-parted, primarily perfect (60 to 75%).

*Flower size.*—Average of 5 mm in diameter and 6 cm in depth.

*Peduncles.*—About 9 cm in length and 2 mm in diameter, 144A in color. glabrous, oval in shape.

*Pedicels.*—About 7 mm in length and 1 mm in diameter, 144A in color, glabrous surface, round in shape.

*Calyx.*—Campanulate in form, comprised of 5 fused sepals, about 5 mm in diameter and 2 mm in depth.

*Sepals.*—5, fused on lower half with apex unfused in triangular shape, acute apex, fused base, 144A in color, glabrous surface with apex region membranous, about 4 mm in length and 1.5 mm in width on unfused portion, entire margin.

*Petals.*—5, un-fused, oblong-ovate in shape but somewhat amorphous, upper and lower surface is membranous, margin irregularly notched, square base, rounded but irregular apex, about 3 cm in length and 2 mm in width, recurved, N144D in color on both surfaces.

Reproductive organs:

*Gynoecium.*—1 pistil emerging from gynandrium, about 4 mm in length and 1.5 mm in width, style is stout, 1 mm in length and width and 144C in color, 4-lobed stigma is 144C in color, ovary is superior, about 1.5 mm in diameter and 144A in color.

*Androcoecium.*—5 stamens, emerging from gynandrium, filaments are 144D in color, about 1.5 mm in length and 0.5 mm in width, anthers are 161B in color and basifixed, pollen was observed on stigma surface only and 165A in color.

*Fruit and seed.*—Fruit; capsules held in clusters about 12 cm in height and 6.5 cm in width, globose in shape, average of 1.4 cm in diameter, glabrous and satiny when green, 144A in color when young in early summer, turns in mid summer to yellow orange; a blending of 12A and N25B and one can discern 4 to 5 sections, matures to bright orange (without sections visible) in late September; 24A in color with a few spots of 139A, fruit skin opens and reflex in October to expose aril that is round, 1.2 cm in diameter, glossy and fleshy in appearance, and 44A to 44C in color, seeds; 2 per berry, elliptic in shape, 4 mm in length and 2.5 mm in diameter, 34A in color. Fruit is persistent.

It is claimed:

1. A new and distinct cultivar of *Celastrus* plant named 'Bailumn' as herein illustrated and described.

* * * * *